United States Patent
Caruba

(10) Patent No.: US 8,387,183 B2
(45) Date of Patent: Mar. 5, 2013

(54) MITIGATION OF BRAKE FAILURE

(75) Inventor: James Frank Caruba, Bartlett, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 13/366,475

(22) Filed: Feb. 6, 2012

(65) Prior Publication Data

US 2012/0136486 A1 May 31, 2012

Related U.S. Application Data

(62) Division of application No. 12/121,033, filed on May 15, 2008, now Pat. No. 8,136,184.

(51) Int. Cl.
*A61G 13/02* (2006.01)
(52) U.S. Cl. .......................................... 5/601; 378/209
(58) Field of Classification Search ...... 5/601; 378/209, 378/208, 205, 20
See application file for complete search history.

(56) References Cited

U.S. PATENT DOCUMENTS

| | | | |
|---|---|---|---|
| 4,885,998 A | 12/1989 | Span et al. | |
| 5,610,968 A | 3/1997 | Deucher et al. | |
| 6,986,179 B2 | 1/2006 | Varadharajulu et al. | |
| 7,125,167 B2 | 10/2006 | Alakkat | |
| 7,607,183 B2 | 10/2009 | Somasundaram et al. | |
| 8,136,184 B2* | 3/2012 | Caruba ........................... | 5/601 |
| 2004/0098804 A1 | 5/2004 | Varadharajulu et al. | |
| 2004/0172758 A1 | 9/2004 | Alakkat | |
| 2007/0080580 A1 | 4/2007 | Narayanasamy | |
| 2007/0107128 A1 | 5/2007 | Somasundaram et al. | |
| 2009/0285364 A1 | 11/2009 | Caruba | |
| 2012/0136486 A1* | 5/2012 | Caruba ........................ | 700/275 |

FOREIGN PATENT DOCUMENTS

EP 1837049 9/2007

* cited by examiner

*Primary Examiner* — Robert G Santos
(74) *Attorney, Agent, or Firm* — Peter Kendall

(57) ABSTRACT

A method and system for mitigations brake failure in a medical device. The method and system includes a motion system for at least one movable load. Each movable load has a drive, a controller for the drive, and a brake. The controller is adapted to monitor positional parameters of the drive or electrical parameters of the brake or a combination of both. The method involves the step of monitoring the parameters and evaluating the parameters to detect a brake failure of the brake.

9 Claims, 6 Drawing Sheets

MITIGATION OF BRAKE FAILURE

CROSS REFERENCE TO RELATED APPLICATIONS

This application is a divisional application of U.S. patent application Ser. No. 12/121,033 filed on May 15, 2008, the disclosure of which is incorporated by reference in its entirety.

TECHNICAL FIELD

The technical field of the present disclosure relates to a method and system for mitigating brake failure for a medical device. More particularly, the hereinafter described method and system relates to detecting brake failure in a medical device, which requires a brake to hold a mechanical load. Brake failure severity and system-level brake failure probability may occur in a medical device carrying load.

BACKGROUND

A medical device may carry a load, such as, for example, a radiation emitting device or a patient. Radiation emitting devices are generally known and used, for instance, as radiation therapy devices for the treatment of patients. A radiation therapy device generally may include a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example.

Another example of a medical device carrying a load is a computed tomography apparatus of the type having a gantry that is rotatable around a rotational axis. An example of such a computed tomography apparatus is disclosed, for example, in U.S. Pat. No. 5,610,968. The computed tomography apparatus has a gantry mounted to be rotatable around a rotational axis and at which the components such as, for example, an X-ray source or a radiation detector that rotate around a patient under examination together with the gantry during operation of the gantry, are arranged.

A further example of a medical device is described in EP 1837049. Such a device comprises at least one drive means (a positioner) for positioning a load, such as a particle beam device. In such a device it is likely that if a system error is detected, then a mechanical brake device will engage and hold the load.

Brake failure in prior art devices and methods is typically mitigated by selecting a "fail-safe" brake and using of a second brake directly on the load. This leads to increasing standard cost in realizing such devices and methods.

A commonly used driving means in the prior art is a ball screw with a single fail-safe brake. For example, for a camera system motion implementation using high efficiency ball screws to move extremely heavy loads with motors driven by amplifiers that are shared with other axes. A single "fail-safe" brake is used to hold the load stationary when, for example, not driven by the motor or during a loss of power. If the brake were to fail, then the load would fall due to the force of gravity acting upon the load. This could result in severe injury.

A load carrying device within the field of medicine for carrying a patient, such as a mechanism moving a patient table top or a bed is known. Such a patient table top is, for example, described in U.S. Pat. No. 4,885,998.

A majority of devices in the prior art typically mitigates brake failure by first selecting of a "fail-safe" brake and thereafter using of a second brake directly on the load. Hereby the standard costs increase.

There are certain prior art camera system motion implementations that employee high efficiency ball screws to move extremely heavy loads with motors driven by amplifiers that are shared with other axes. A single "fail-safe" brake is used to hold the load stationary when not driven by the motor or during a loss of power. If the brake were to fail, then the load would fall due to the force of gravity acting upon the load and severe injury could result. When considering the possible failure modes of a single "fail-safe" brake implemented in a ball-screw driven axis (such as the radial axis), the associated system response may be one or more of the following:

(A) Brake fails to release. This may result in no hazard.
(B) Brake fails to engage at the end of movement. This may result in that the motion system kills power upon detection of unintended motion and the load falls.
(C) Brake holding power degrades over time, resulting in slippage. This may result in that the motion system kills power and the load either comes to a stop after moving a greater than expected distance or slowly falls due to continuous brake slippage.
(D) Catastrophic brake failure, with the system powered, stationary and not in a stationary state, resulting in unintended release of the load. This may result in the load falling.
(E) Catastrophic brake failure, with the system not powered, or in a stationary state, resulting in unintended release of the load. This may result in the load falling.

In view of the prior art discussed above, there is a need to provide a method and system allowing for a more safe manner to mitigate brake failure. Additionally, such a method and system should preferably be inexpensive to realize. There is also a need to improve the mitigation of brake failure in existing devices. This would allow for a safe medical device carrying loads without causing any mechanical damage or personal injury.

There is a need that existing methods and systems taking advantage of existing system motion features could result in a more accurate positioning of medical devices in relation to patients, because improved reliability and accuracy of a brake system. Good spatial information of the relevant part of the medical device needs to be assessed. Hereby patients could be treated in a more target-specific manner resulting in, for example, reduced radiation dosage when X-rayed.

There also exists a need to minimize the structure of the medical device by avoiding the need for extra safety devices, such as extra brakes. The construction of the medical device should be simple from a technical and an economical perspective.

Additionally, it is desirable to avoid cumbersome arrangements that would interfere with the available space around the medical device.

SUMMARY

According to an embodiment, a medical device may comprise a motion system for at least one movable load and for each movable load drive means, control means for the drive means, and brake means. The control means may be adapted to detect a brake failure of the brake means by monitoring positional parameters of the drive means or electrical parameters of the brake means or a combination of both.

According to further embodiments, the control means may be adapted to respond with at least one of the following in response to the monitoring of the parameters: enable the drive means for the movable load with the brake failure; retract any patient pallet from the motion system; retract the movable load with the brake failure away from any possible area occupied by a person; or position the movable load with the brake failure in a position such that gravity will not cause the load to move.

According to further embodiments, the control means may be adapted to monitor: a stop position P1 of the drive means; a stop position P2 after the drive means stopped and engagement of the break means; and a stop position P3 T seconds after engagement of the break means. Furthermore, the control means may be adapted to evaluate the difference between positions P1 and P2 and the difference between positions P2 and P3, either on a statistical basis or on a specific basis by calibration for each specific drive means.

According to further embodiments, the control means may be adapted to monitor: a stop position P3 T seconds after engagement of the break means; and a stop position P4 before the next move of the load by the drive means. Furthermore, the control means may be adapted to evaluate the difference between positions P3 and P4, either on a statistical basis or on a specific basis by calibration for each specific drive means.

According to further embodiments, the control means may be adapted to monitor all stop positions when the motion system is in a stationary state. Furthermore, the control means may be adapted to evaluate all stop positions to detect any movement in any drive means beyond a specific tolerance.

According to further embodiments, the control means may be adapted to monitor a group of electrical brake operating parameters. Furthermore, the control means is adapted to evaluate the electrical brake operating parameters to detect any movement in any drive means.

In further embodiments, the medical device may be selected from the group consisting of: X-ray apparatus; a CT scanner; a vascular imaging apparatus; an apparatus for radiation diagnosis; an apparatus for radiation therapy; a SPECT Gamma Camera; or similar devices.

In further embodiments, the load may be selected from the group consisting of: a medical imaging apparatus; a gantry; a patient table with or without a patient; or any other load in the medical device.

In further embodiments, the control means may be selected from the group consisting of: a numerical controller; a computer; an electrical device; or a mechanical device.

In further embodiments, the drive means may be a linear drive, a rotational drive, or a combination thereof and the drive means may be driven by a ball screw, amplifier, fluid pressure, pneumatic power, or any other mechanical or electrical drive.

In further embodiments, the brake means may be selected from the group consisting of: fluid pressure brake; pneumatic brake; electric brake; magnetic brake; mechanical brake; or similar brake.

According to an embodiment, a method may mitigate brake failure in a medical device. The medical device may comprise a motion system for at least one movable load, and for each movable load drive means, control means for the drive means, and brake means. The control means may be adapted to monitor positional parameters of the drive means or electrical parameters of the brake means or a combination of both. The method may comprise the steps of monitoring the parameters and evaluating the parameters to detect a brake failure of the brake means.

In further embodiments, the control means may respond with at least one of the following upon detection of a brake failure: enabling the drive means for the movable load with the brake failure; retracting any patient pallet from the motion system; retracting the movable load with the brake failure away from any possible area occupied by a person; or positioning the movable load with the brake failure in a position such that gravity will not cause the load to move.

In further embodiments, the control means may monitor a stop position P1 of the drive means; a stop position P2 after the drive means stopped and engagement of the break means; and a stop position P3 T seconds after engagement of the break means. Further, the control means may evaluate the difference between positions P1 and P2 and the difference between positions P2 and P3, either on a statistical basis or on a specific basis by calibration for each specific drive means.

In further embodiments, the control means may monitor a stop position P3 T seconds after engagement of the break means; and a stop position P4 before the next move of the load by the drive means. Further, the control means may evaluate the difference between positions P3 and P4, either on a statistical basis or on a specific basis by calibration for each specific drive means.

In further embodiments, the control means monitoring all stop positions when the motion system is in a stationary state and the control means may evaluate all stop positions to detect any movement in any drive means beyond a specific tolerance.

In further embodiments, the control means monitoring a group of electrical brake operating parameters, and the control means may evaluate the electrical brake operating parameters to detect any movement in any drive means.

According to an embodiment, a method may mitigate brake failure in a medical device. The medical device may comprise a motion system for at least one movable load, and for each movable load a linear or rotational drive, a numerical controller, and a brake. The numerical controller may be adapted to monitor positional parameters of the linear or rotational drive or electrical parameters of the brake or a combination thereof. The method may comprise the steps of monitoring the parameters, evaluating the parameters to detect a brake failure of the brake, and responding with at least one of the following upon detection of a brake failure: enabling the linear or rotational drive for the movable load with the brake failure; retracting any patient pallet from the motion system; retracting the movable load with the brake failure away from any possible area occupied by a person; or positioning the movable load with the brake failure in a position such that gravity will not cause the load to move.

In further embodiments, the numerical controller may monitor at least one of the following positional parameters of the linear or rotational drive: a stop position P1; a stop position P2 after the linear or rotational drive stopped and engagement of the break; a stop position P3 T seconds after engagement of the break means; a stop position P4 before the next move of the load by the linear or rotational drive; or a stop position when the motion system is in a stationary state. Further, the numerical controller may evaluate at least one of the positions, either on a statistical basis or on a specific basis by calibration for each specific drive, to detect a brake failure.

In further embodiments, the numerical controller may monitor at least one electrical parameter of at least one brake of the motion system, and the numerical controller may evaluate at least one electrical parameter to detect any movement in any linear or rotational drive.

At least one embodiment of the present invention provides a method and system for a safer manner to mitigate brake failure. Additionally, such a method and system may be inexpensive to realize. Embodiments improve the mitigation of brake failure in existing devices. This allows for a safe medical device carrying loads without causing any mechanical damage or personal injury.

A method and system according to at least one embodiment take advantage of existing system motion features. At least one embodiment of the present invention results in a more accurate positioning of medical devices in relation to patients, because of improved reliability and accuracy of the brake system. As a result, good spatial information of the relevant part of the medical device can be assessed. Hereby patients can be treated in a more target-specific manner resulting in, for example, reduced radiation dosage when X-rayed.

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any preceding claimed embodiment(s).

BRIEF DESCRIPTION OF THE DRAWINGS

The accompanying drawings, which are incorporated in and constitute a part of the specification, illustrate presently preferred embodiments, and together with the general description given above and the detailed description of the preferred embodiments given below, serve to explain, by way of example, the principles of the invention.

DETAILED DESCRIPTION

The hereinafter described embodiments may provide a device and method allowing for mitigation of brake failure. By detecting brake failure mechanical damage or human injury may be avoided. Additionally, by detecting, for example, brake slippage in the hereinafter described embodiments a more accurate positioning of medical devices in relation to patients may be achieved. Therefore, good spatial information of the relevant part of the patient can be assessed. Hereby patients may be treated in a more target-specific manner resulting in, for example, reduced radiation dosage when X-rayed.

The hereinafter described embodiments may further provide a device and method minimizing the structure of the medical device by avoiding the need for extra safety devices, such as extra brakes. The construction of the medical device according to the hereinafter described embodiments provides for high efficiency at low costs. Additionally, the hereinafter described embodiments may avoid cumbersome arrangements that would interfere with the available space around the medical device.

A problem may be that the use of a second brake directly on the load may cause increased costs and cumbersome arrangements. Consequently, an alternative way of mitigating brake failure is sought.

According to an embodiment a multi-axis motion system controller is used to monitor the positions of all axes at all times by tracking positions of incremental encoders and uses motors attached to all of the axes of the multi-axis motion system controller and may detect and intervene during a brake failure. The hereinafter described embodiments may be implemented completely within software, firmware, or hardware and may be deployed to an installed camera case, or similar.

The probability and severity of brake failure can be reduced by taking advantage of existing system-level motion system features as a means of brake failure detection and mitigation.

With regard to the possible failure modes of a single "fail-safe" brake implemented in a ball-screw driven axis and the possible associated system responses, as discussed in the prior art, embodiments may mitigate brake failure. Failure mode (A) presents no hazard. Failure modes (B) through (D) can be mitigated by various embodiments. Also, the probability of Failure Mode (E) can be reduced by various embodiments.

According to an embodiment brake failure is mitigated by first placing a medical device in a mechanically balanced safe state, secondly automatically extracts the patient pallet, and thirdly disables the system from any further motion. Hereby mitigation of axis primary brake failure is achieved.

Figure 1:
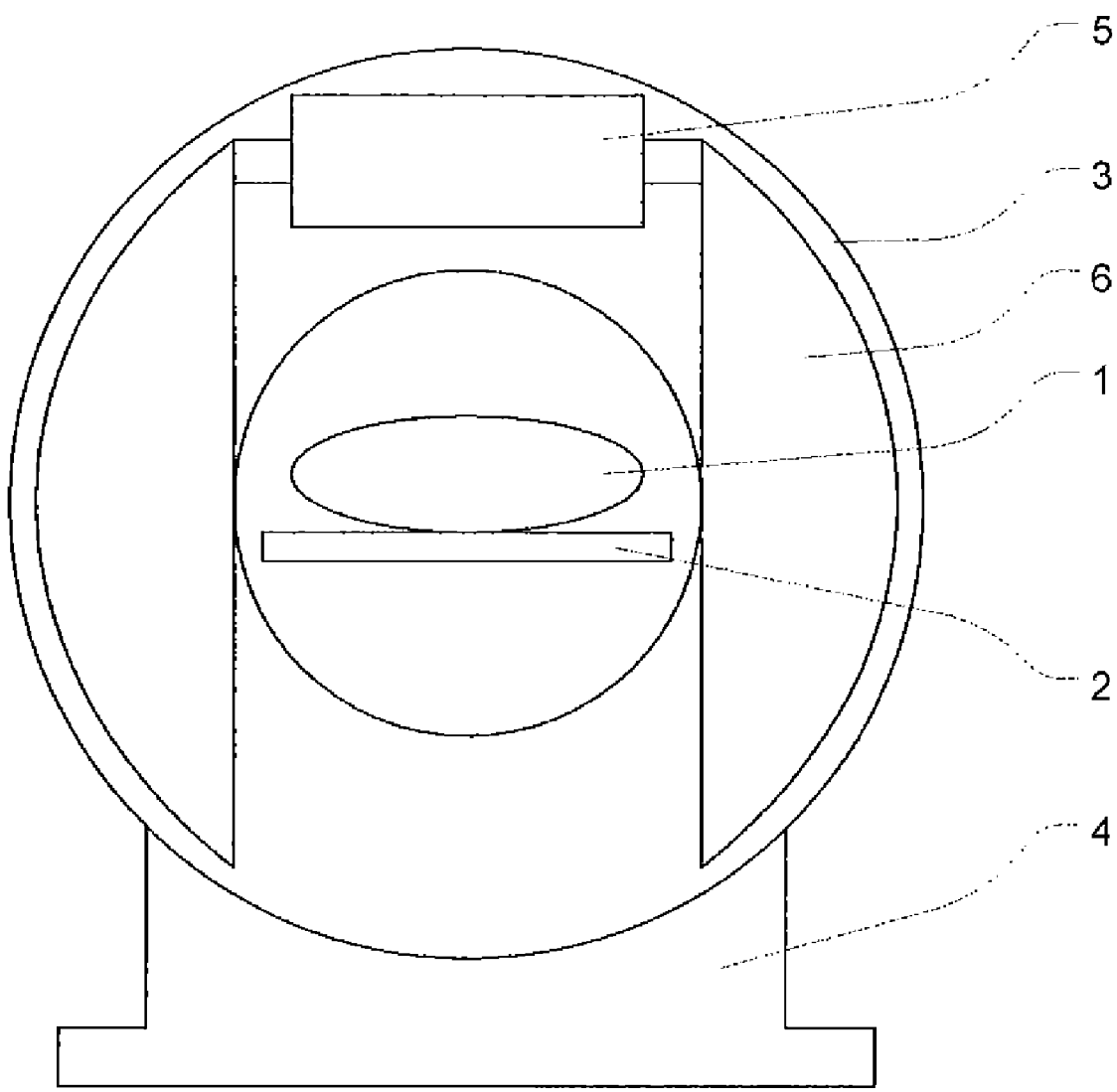
FIG. 1 shows a schematic drawing of an example of a medical device suitable for being used with at least one embodiment exemplary.

FIG. 1 shows a schematic drawing of an example of a medical device suitable for being used according to one embodiment. Such an example of a medical device may be any medical device carrying a load. The medical device may be, for example, an X-ray apparatus, a CT scanner, a vascular imaging apparatus, an apparatus for radiation diagnosis, an apparatus for radiation therapy, a SPECT detector, or similar devices.

The medical device in FIG. 1 shows a patient 1 on a patient table top 2. These are positioned relative to the medical device such that an operation can be performed on the patient. The patient table top 2 carries a load, namely the patient 1 and the patient table top 2 itself. The drive means of a patient table top may have a brake to hold the patient table top 2. Embodiments of the present invention may be suitable to mitigate brake failure of drive means for such a patient table top. The medical device may comprise a gantry 3 on a stand 4. The gantry 3 may carry a motion guide 6, which in turn carries a load, such as, for example, a SPECT detector 5. The drive means of the radiation emitting device 5 may have a brake to hold the radiation emitting device 5. Embodiments of the present invention may be suitable to mitigate brake failure of drive means for such a load. The drive means may comprise a single motor with or without an associated transmission gear for driving the load. However, the drive means may also encompass a shared drive with for example, two motors driven at different times by the same drive & control sequencer. Other drive means can be implemented with more than two motors and if necessary respective transmission gears.

Figure 2:
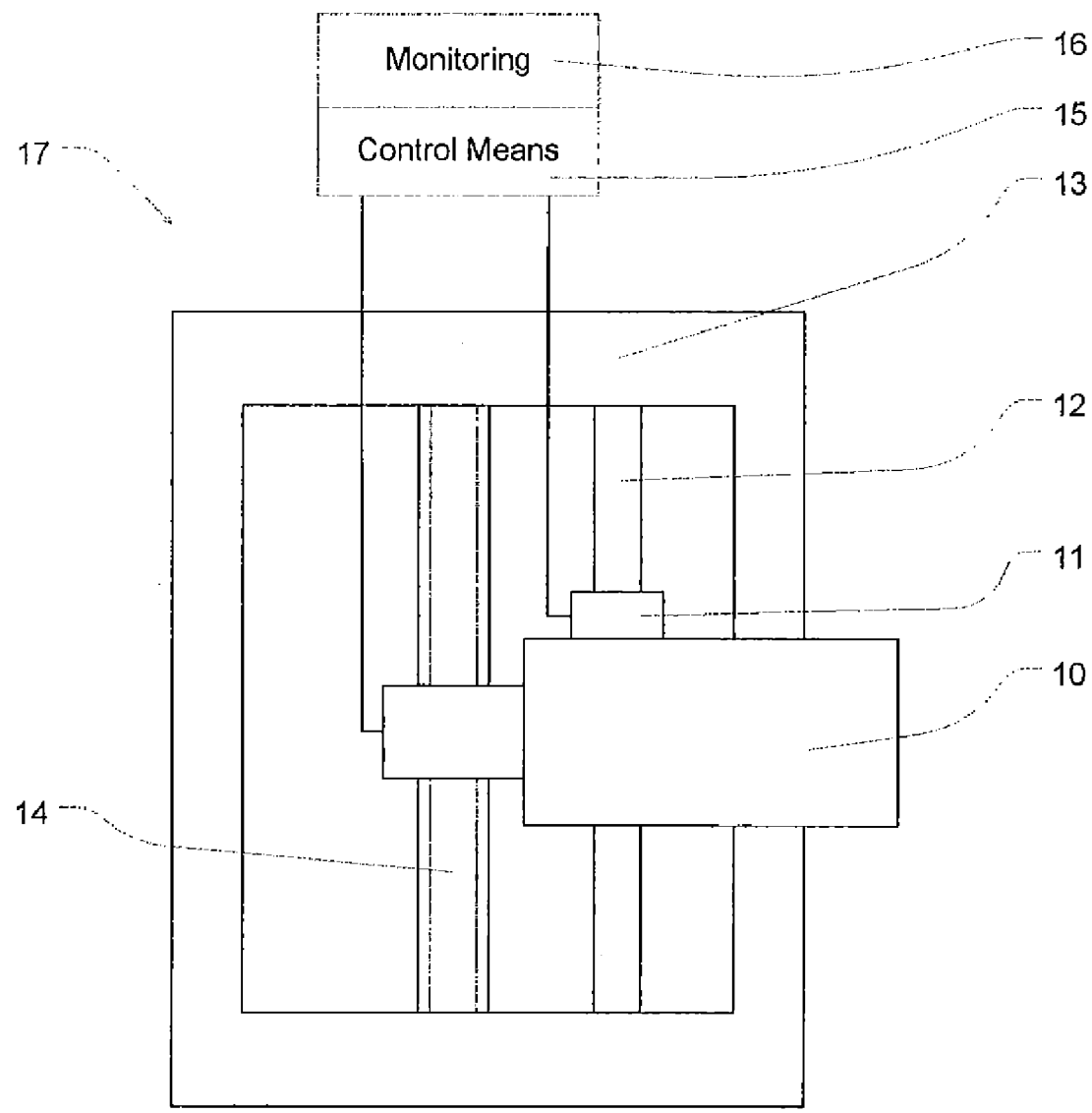
FIG. 2 shows a schematic drawing of an example of a motion system for a medical device according to one embodiment.

FIG. 2 shows a schematic drawing of an example of a motion system 17 for a medical device according to one embodiment. The motion system could be, for example, the motion guide 6 in FIG. 1. A part 13 of the medical device comprises drive means, such as, for example, a ball screw 14. The drive means may be, for example, a linear drive, a rotational drive, or a combination thereof and the drive means may be driven by, for example, a ball screw, an amplifier, fluid pressure, pneumatic power, or any other mechanical or electrical drive. The ball screw 14 drives a load 10. This load may be, for example, a medical imaging apparatus, a gantry, a patient table with or without a patient, or any other load in the medical device. The part 13 of the medical device may further comprise guide means, such as a linear guide 12. It is however not necessary that the part 13 of the medical device comprises guide means beside the drive means. Brake means 11 may be provided on the guide 12. The brake 12 may be provided on any other suitable part, such as the drive means or a part of the medical device. The brake 12 may be, for example, a fluid pressure brake, a pneumatic brake, an electric brake, a magnetic brake, a mechanical brake, or similar brake.

Control means 15 and monitoring means 16 may be connected to the drive means and the brake means. The control means may be a numerical controller, a computer, an electrical device, or a mechanical device. This control means may control the movement and positioning of the load. The monitoring means may monitor the movements and positions of the load. The drive means is controlled by the control means 15. In this way a linear drive, a rotational drive, or a combination thereof may be controlled in the medical device to move or position a load.

In one embodiment the control means 15 may be adapted to monitor a group of electrical brake operating parameters. The control means 15 may be adapted to evaluate the electrical brake operating parameters to detect any movement in any drive means. This may be a way of detecting a brake failure.

In one embodiment the control means 15 may be adapted to monitor positional parameters of the drive means. The control means 15 may be adapted to evaluate the positional parameters to detect any movement in any drive means. This may be another way of detecting a brake failure of the brake means.

The control means 15 in embodiments of the present invention may be adapted to monitor positional parameters of the drive means in combination with being adapted to monitor a group of electrical brake operating parameters. The control means 15 may be adapted to evaluate the positional parameters in combination with being adapted to evaluate the group of electrical brake operating parameters to detect any movement in any drive means. This may be yet another way of detecting a brake failure of the brake means.

A medical device may in one embodiment comprise a motion system 17 for at least one movable load 10. The motion system 17 may, comprising for each movable load 10 drive means, such as the ball screw 14, control means 15 for the drive means, and brake means 11. The control means 15 may be adapted to detect a brake failure of the brake means 11 by monitoring positional parameters of the drive means or electrical parameters of the brake means 11 or a combination of both. In this way the brake performance on, for example, a high efficiency camera motion axis may be tracked parametrically to mitigate brake failure severity and reduce the probability of brake failure at a system-level. The motion axis, for example a linear or rotational drive, may use a brake to hold the load of the high efficiency camera from moving during loss of power or sharing of a motor drive, such as an amplifier.

Figure 3:
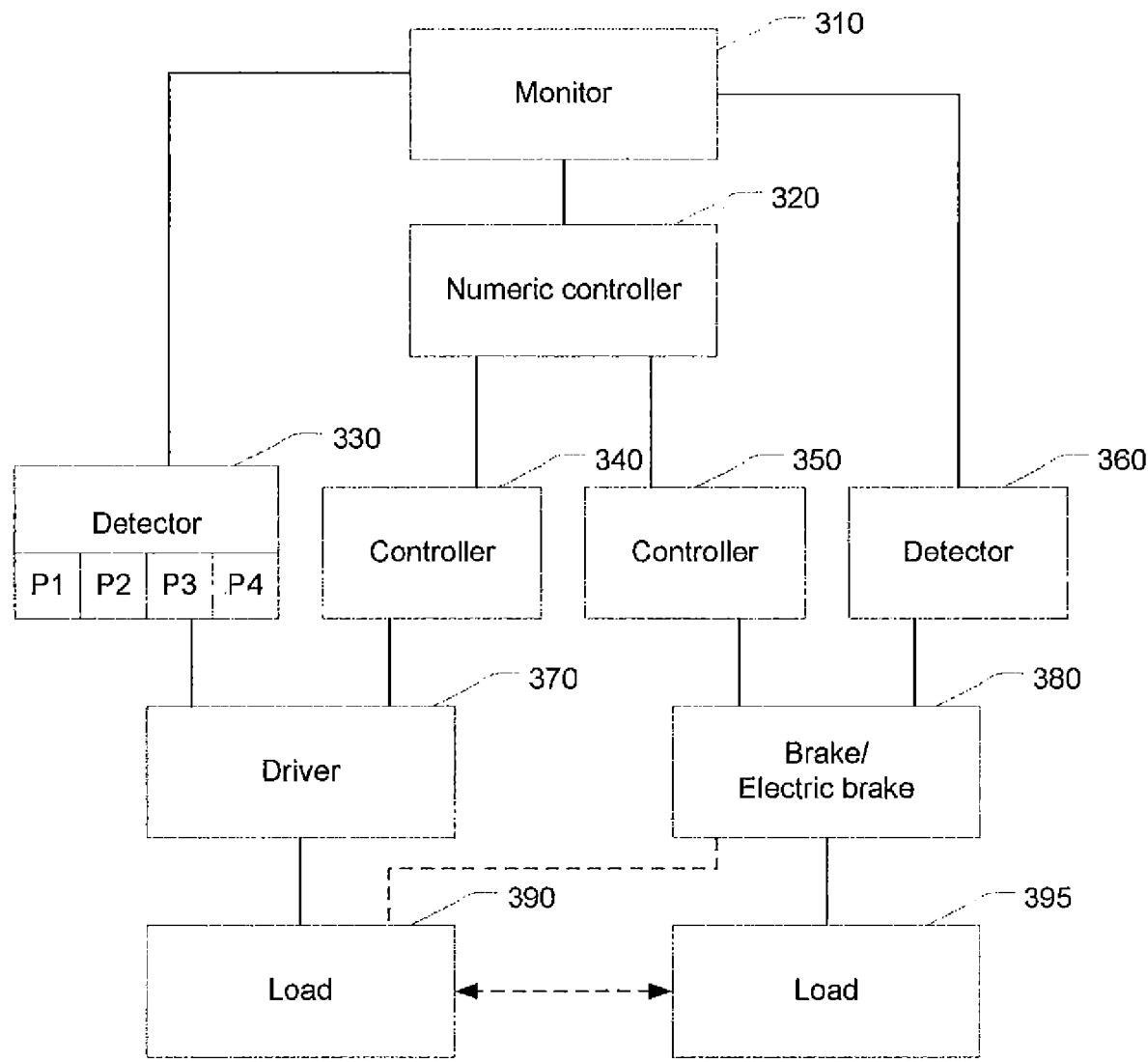
FIG. 3 shows a diagram of an embodiment.

Turning to FIG. 3, a diagram of an embodiment of a system 300 is shown. Here the numeric controller 320 may control a drive 370 and a brake 380 via respective controllers 340, 350. The brake 380 may be an electric or mechanical brake. The driver 370 drives a load 390 and the brake may break the same load 390 or another load 395 in connection with the driven load. A detector 330 detects, for example, positional parameters of the drive 370. These positional parameters could be, for example, different stop positions P1, P2, P3, and/or P4. A monitor 310 may be connected to the detector 330 of the driver 370 for monitoring parameters of the drive 370. These parameters are feed to the numeric controller 320. By analyzing and monitoring the parameters a possible brake failure may be mitigated. The analyzing or monitoring could, for example, be made by comparing the parameters with themselves, with other parameters, or with fixed preset parameters.

If the parameters are positions, the analyzing or monitoring could, for example, be made by tracking the difference between positions. The difference may be tracked either on a statistical basis across all like axis or on a specific basis by calibration for the specific axis in question. The difference may then indicate a brake failure.

In a further embodiment, all stop positions when the motion system is in a stationary state may be monitored. By evaluating all stop positions, the numeric controller 320 may detect any movement in any drive means beyond a specific tolerance. Hereby a possible brake failure may be mitigated.

A detector 360 may also or instead be detecting parameters of the brake 380. These parameters could be, for example, a group of electrical brake operating parameters. The monitor 310 may be connected to the detector 360 of the brake 380 for monitoring parameters of the brake 380. These parameters are feed to the numeric controller 320. By analyzing and monitoring the parameters a possible brake failure may be mitigated. The analyzing or monitoring could, for example, be made by evaluating the electrical brake operating parameters to detect any movement in any drive means. Hereby a possible brake failure may be mitigated.

Figure 4:
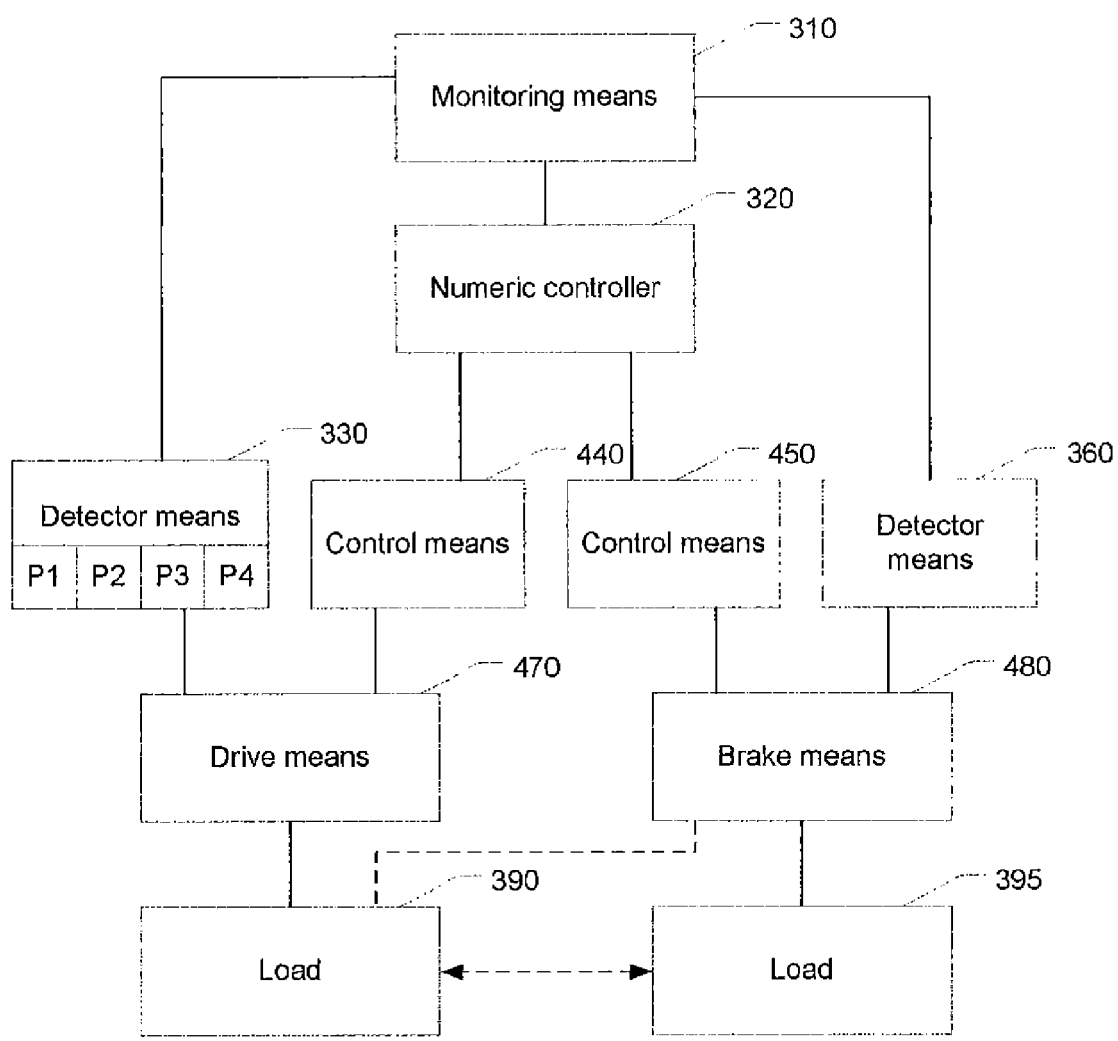
FIG. 4 shows a diagram of another embodiment.

FIG. 4 shows a diagram of another embodiment. This embodiment resembles that embodiment shown in FIG. 3. Even if the diagram is drawn out in a fairly similar way, the components of the medical device and its motion system may differ. The control means 440, 450 may, for example, be a numerical controller, a computer, an electrical device, or a mechanical device. The drive means 470, 480 may be, for example, a linear drive, a rotational drive, or a combination thereof and the drive means may be driven by a ball screw, amplifier, fluid pressure, pneumatic power, or any other mechanical or electrical drive. The brake means 480 may be, for example, a fluid pressure brake, pneumatic brake, electric brake, magnetic brake, mechanical brake, or similar brake.

Turning now to an embodiment exemplifying how positional parameters may mitigate brake failure, three positional parameters may be monitored. This embodiment may apply when the drive 370 or drive means 470 in FIG. 3 or 4 comes to an end. A first position of the drive means may be the stop position P1 of the drive means. A second position of the drive means may be a stop position P2 after the drive means stopped and the break means has engaged. A third position of the drive means may be a stop position P3 a certain amount T of seconds after engagement of the break means. Monitoring the difference between positions P1 and P2 and the difference between positions P2 and P3, either on a statistical basis across all like axis or on a specific basis by calibration for the specific axis in question, may detect failure modes (B) and (C). Upon detection of failure mode (B) or (C) the motion system may, for example, (1) re-enable the drive means, (2) retract the patient pallet from the medical device if applicable, (3) retract the drive means or load away from the patient if applicable and (4) position the medical device such that the drive means with the brake failure is in a balanced position and not caused to move by the force of gravity.

By adapting the control means to monitor the stop position P1 of the drive means; the stop position P2 after the drive means stopped and engagement of the break means; and the stop position P3 T seconds after engagement of the break means; and adapting the control means to evaluate the difference between positions P1 and P2 and the difference between positions P2 and P3, either on a statistical basis or on a specific basis by calibration for each specific drive means, brake failure may be mitigated.

Turning now to a further embodiment exemplifying how positional parameters may mitigate brake failure, two positional parameters may be monitored. This embodiment may apply when the drive 370 or drive means 470 in FIG. 3 or 4 comes to an end and/or begins to move. A position of the drive means may be the stop position P3 a certain amount T of seconds after engagement of the break means. A further position of the drive means may be the stop position P4 at the beginning of next move of the drive means. Monitoring the difference between positions P3 and P4, either on a statistical basis across all like axis or on a specific basis by calibration for the specific axis in question, can detect a failure mode (C). Upon detection of a failure mode (C) the motion system may, for example, (1) re-enable the drive means, (2) retract the patient pallet from the medical device if applicable, (3) retract the drive means or load away from the patient if applicable and (4) position the medical device such that the drive means with the brake failure is in a balanced position and not caused to move by the force of gravity.

By adapting the control means to monitor the stop position P3 T seconds after engagement of the break means; and the stop position P4 before the next move of the load by the drive means, and adapting the control means to evaluate the difference between positions P3 and P4, either on a statistical basis or on a specific basis by calibration for each specific drive means, brake failure may be mitigated.

Turning now to a further embodiment exemplifying how positional parameters may mitigate brake failure, all positional parameters may be monitored. This embodiment may apply when the drive means in FIG. 3 or 4 are in a powered stationary state. Monitoring the stationary positions of all drives may detect failure mode (D), if any positional parameter moves beyond a specified tolerance. Upon detection of failure mode (D) the motion system may, for example, (1) re-enable the drive means, (2) retract the patient pallet from the medical device if applicable, (3) retract the drive means or load away from the patient if applicable and (4) position the medical device such that the drive means with the brake failure is in a balanced position and not caused to move by the force of gravity.

By adapting the control means to monitor all stop positions when the motion system is in a stationary state; and adapting the control means to evaluate all stop positions to detect any movement in any drive means beyond a specific tolerance, brake failure may be mitigated.

If a brake failure is detected, embodiments of the medical device may respond in at least one, or in any combination, of the following. (1) Enable the drive means for the movable load with the brake failure. (2) Retract any patient pallet from the motion system. (3) Retract the movable load with the brake failure away from any possible area occupied by a person. (4) Position the movable load with the brake failure in a position such that gravity will not cause the load to move.

In one embodiment the medical device may mitigate brake failure and respond by first placing the system in a mechanically balanced safe state, secondly automatically extracting the patient pallet and thirdly disabling the system from any further motion.

Turning to failure mode (E), embodiments may detected failure mode (E) but may not mitigate failure mode (E) by positioning the gantry into a balanced state, because motion power is disabled while in a stationary state. However, the probability of failure mode (E) may be reduced through the evaluation of the parameter outlined above, since one would expect some degradation in brake performance prior to catastrophic failure.

In a further embodiment of the medical device, the above motion system interventions may be attempted for a fixed period of time, to mitigate drive means failure resulting in driving the respective drive means through the brake means in the direction of gravity. An appropriate response may be to cut the power to the motion system.

Any of the above outlined evaluation and monitoring of any parameters outlined above may be used in any combination to reduce the severity and system-level probability of a brake failure in order to improve the overall brake failure hazard.

Figure 5:
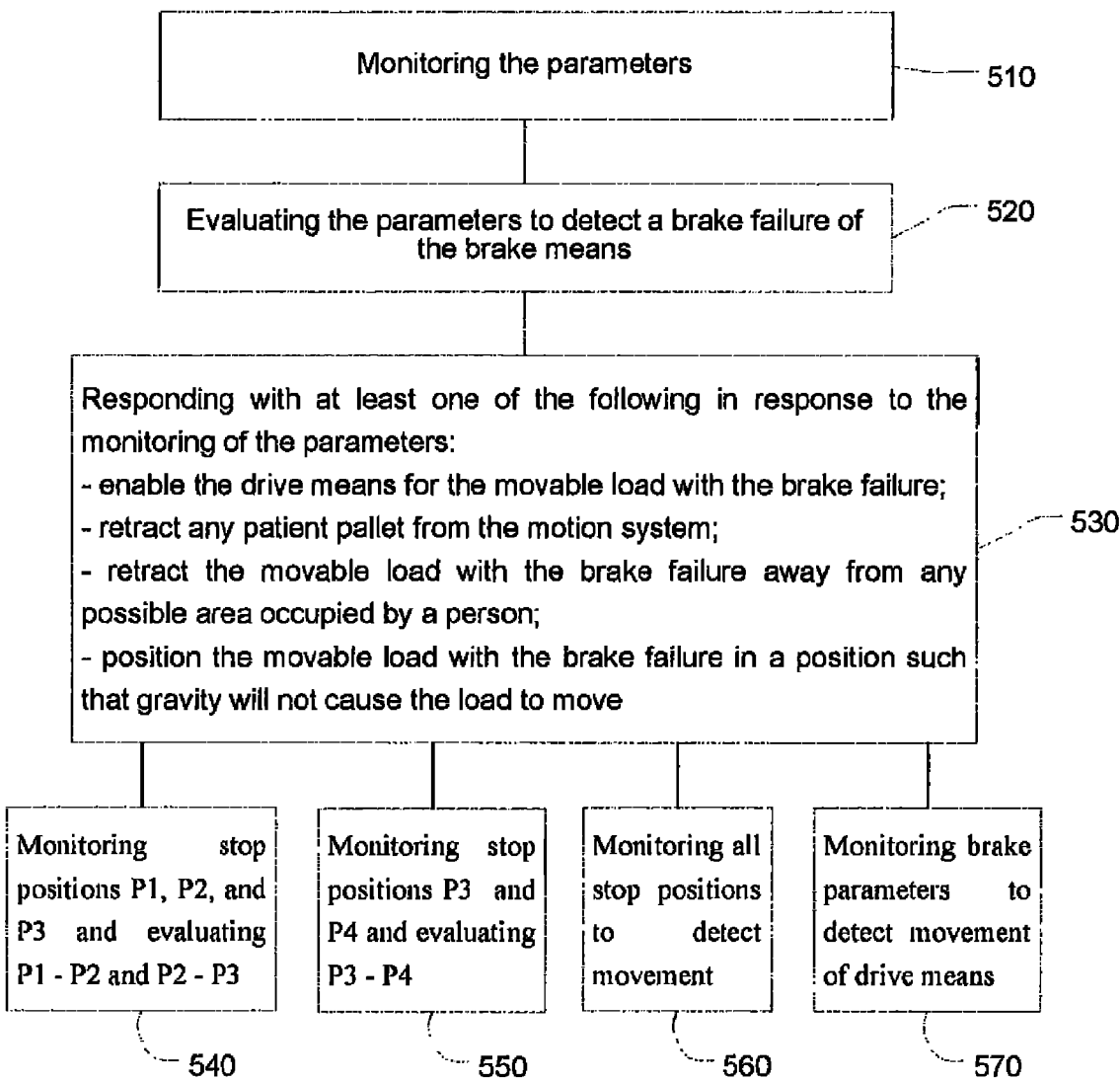
FIG. 5 shows a flow chart of a method for mitigating brake failure according to an embodiment.

FIG. 5 shows a flow chart of a method for mitigating brake failure according to an embodiment. The method may mitigate brake failure for a medical device with a motion system for at least one movable load. Each movable load may have drive means, control means for the drive means, and brake means. The control means may be adapted to monitor positional parameters of the drive means or electrical parameters of the brake means or a combination of both.

The method according to this embodiment may have the following steps. In step 510 the parameters are monitored. In step 520, the parameters are evaluated to detect a brake failure of the brake means.

In one embodiment, a third step 530 may be the control means responding with at least one of the following upon detection of a brake failure: enabling the drive means for the movable load with the brake failure; retracting any patient pallet from the motion system; retracting the movable load with the brake failure away from any possible area occupied by a person; or positioning the movable load with the brake failure in a position such that gravity will not cause the load to move.

In a further embodiment, the control means may in step 540 monitor a stop position P1 of the drive means, a stop position P2 after the drive means stopped and engagement of the break means, and a stop position P3 T seconds after engagement of the break means, and the control means may evaluate the difference between positions P1 and P2 and the difference between positions P2 and P3, either on a statistical basis or on a specific basis by calibration for each specific drive means.

In still a further embodiment, the control means may in step 550 monitor a stop position P3 T seconds after engagement of the break means, and a stop position P4 before the next move of the load by the drive means, and the control means may evaluate the difference between positions P3 and P4, either on a statistical basis or on a specific basis by calibration for each specific drive means.

In still a further embodiment, the control means may in step 560 monitor all stop positions when the motion system is in a stationary state, and the control means may evaluate all stop positions to detect any movement in any drive means beyond a specific tolerance.

In yet another embodiment, the control means may in step 570 monitor a group of electrical brake operating parameters, and the control means may evaluate the electrical brake operating parameters to detect any movement in any drive means.

Figure 6:
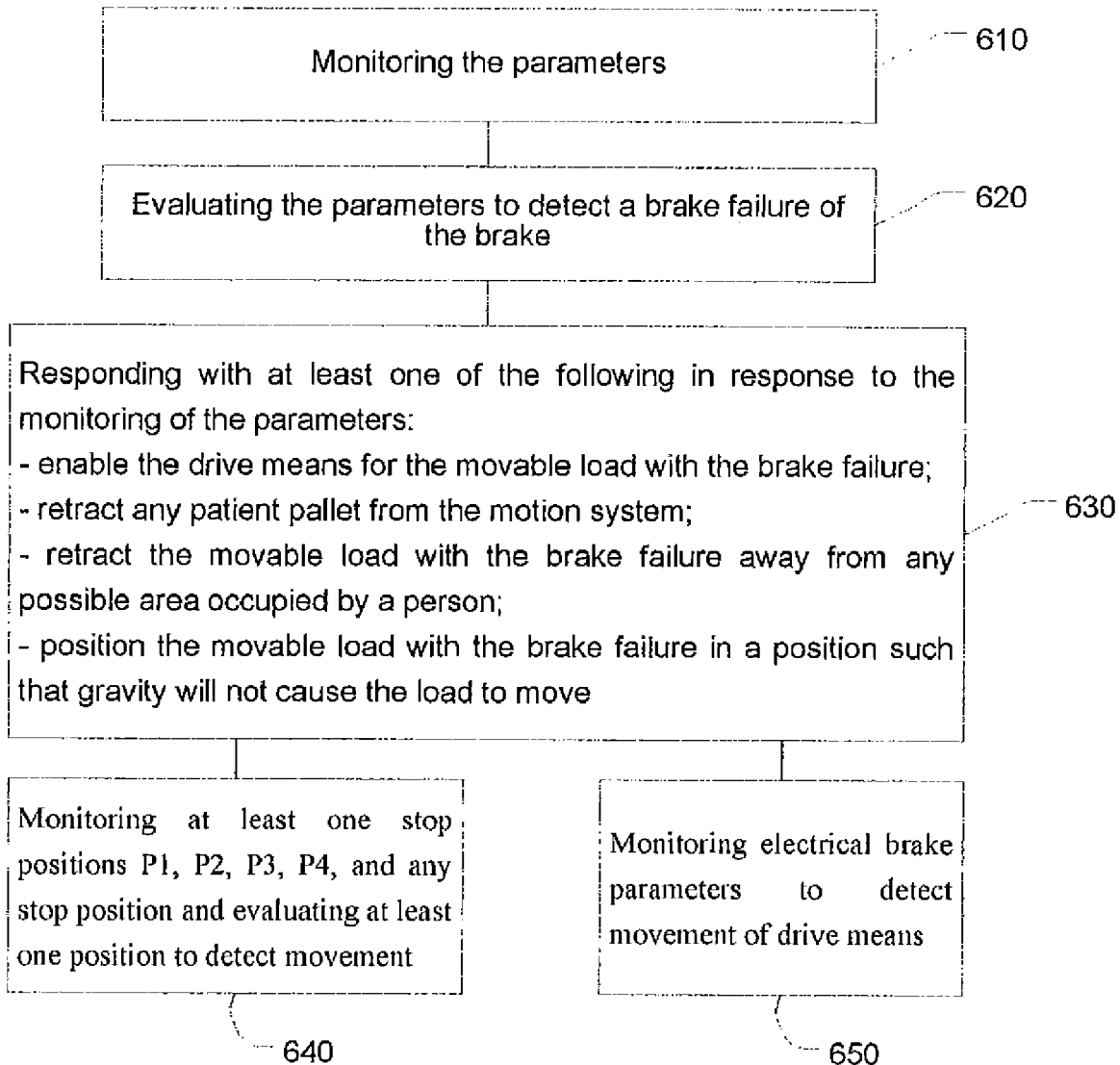
FIG. 6 shows a flow chart of a method for mitigating brake failure according to an embodiment.

FIG. 6 shows a flow chart of a method for mitigating brake failure according to an embodiment. The method may mitigate brake failure for a medical device with a motion system for at least one movable load. Each movable load may have a linear or rotational drive, a numerical controller for the drive means, and a brake. The numerical controller may be adapted to monitor positional parameters of the linear or rotational drive or electrical parameters of the brake or a combination of both.

The method according to this embodiment may have the following steps. The parameters are monitored in step 610. Secondly, in step 620, the parameters are evaluated to detect a brake failure of the brake. Thirdly, in step 630, the numerical controller may respond with at least one of the following upon detection of a brake failure: enabling the linear or rotational drive for the movable load with the brake failure; retracting any patient pallet from the motion system; retracting the movable load with the brake failure away from any possible area occupied by a person; or positioning the movable load with the brake failure in a position such that gravity will not cause the load to move.

In a further embodiment, the numerical controller may in step 640 monitor at least one of the following positional parameters of the linear or rotational drive: a stop position P1; a stop position P2 after the linear or rotational drive stopped and engagement of the break; a stop position P3 T seconds after engagement of the break means; a stop position P4 before the next move of the load by the linear or rotational drive; a stop position when the motion system is in a stationary state; and the numerical controller may evaluate the at least one position, either on a statistical basis or on a specific basis by calibration for each specific drive, to detect a brake failure.

In a further embodiment, the numerical controller may in step 650 monitor at least one electrical parameter of at least one brake of the motion system, and the numerical controller may evaluate the at least one electrical parameter to detect any movement in any linear or rotational drive.

The device and method discussed above mitigates brake failure for a medical device. The disclosure, therefore, is well adapted to carry out the objects and attain the ends and advantages mentioned, as well as others inherent therein. While the disclosure has been described and is defined by reference to particular preferred embodiments, such references do not imply a limitation, and no such limitation is to be inferred. The disclosure is capable of considerable modification, alteration, and equivalents in form and function, as will occur to those ordinarily skilled in the pertinent arts. The described preferred embodiments are exemplary only, and are not exhaustive of the scope of the disclosure. Consequently, the disclosure is intended to be limited only by the spirit and scope of the appended claims, giving full cognizance to equivalents in all respects.

What is claimed is:

1. A method for mitigating brake failure in a medical device, wherein the medical device has a motion system for at least one movable load, and each movable load having: drive means, control means for the drive means, and brake means, wherein the control means is adapted to monitor positional parameters of the drive means or electrical parameters of the brake means or a combination of both;
   the method comprising the following steps:
   monitoring the parameters;
   evaluating the parameters to detect a brake failure of the brake means; and
   placing the brake means in a balanced state such that gravity will not cause the load to move upon detection of the brake failure.

2. The method according to claim 1, further comprising the steps of the control means responding with at least one of the following upon detection of a brake failure:
   enabling the drive means for the movable load with the brake failure;
   retracting any patient pallet from the motion system; and
   retracting the movable load with the brake failure away from any possible area occupied by a person.

3. The method according to claim 2, further comprising the steps of the control means monitoring:
   a stop position (P1) of the drive means;
   a stop position (P2) after the drive means stopped and engagement of the brake means; and
   a stop position (P3) at a time (T) after engagement of the brake,
   wherein the control means evaluating the difference between positions P1 and P2 and the difference between positions P2 and P3, either on a statistical basis or on a specific basis by calibration for each specific drive means.

4. The method according to claim 3, further comprising the steps of the control means monitoring:
   a stop position (P3) at a time (T) after engagement of the brake; and
   a stop position (P4) before the next move of the load by the drive means,
   wherein the control means evaluating the difference between positions P3 and P4, either on a statistical basis or on a specific basis by calibration for each specific drive means.

5. The method according to claim 2, further comprising the steps of the control means monitoring all stop positions when the motion system is in a stationary state; and
   the control means evaluating all stop positions to detect any movement in any drive means beyond a specific tolerance.

6. The method according to claim 2, further comprising the steps of the control means monitoring a group of electrical brake operating parameters; and
   the control means evaluating the electrical brake operating parameters to detect any movement in any drive means.

7. A method for mitigating brake failure in a medical device, the medical device having a motion system for at least one movable load, each movable load having a linear or rotational drive, a numerical controller, and a brake, wherein the numerical controller is adapted to monitor positional parameters of the linear or rotational drive or electrical parameters of the brake or a combination thereof;
   the method comprising the following steps:
   monitoring the parameters;
   evaluating the parameters to detect a brake failure of the brake; and
   placing the brake in a balanced state such that gravity will not cause the load to move upon detection of the brake failure.

8. The method according to claim 7, further comprising the steps of the numerical controller monitoring at least one of the following positional parameters of the linear or rotational drive:
   a stop position (P1);
   a stop position (P2) after the linear or rotational drive stopped and engagement of the brake;
   a stop position (P3) at a time (T) after engagement of the brake;
   a stop position (P4) before the next move of the load by the linear or rotational drive;
   a stop position when the motion system is in a stationary state; and
   the numerical controller evaluating the at least one position, either on a statistical basis or on a specific basis by calibration for each specific drive, to detect a brake failure.

9. The method according to claim 7, further comprising the steps of the numerical controller monitoring at least one electrical parameter of at least one brake of the motion system; and
   the numerical controller evaluating the at least one electrical parameter to detect any movement in any linear or rotational drive.

* * * * *